United States Patent
Cude

(10) Patent No.: US 8,770,409 B2
(45) Date of Patent: Jul. 8, 2014

(54) DUAL PACK CONTAINER

(75) Inventor: J. Michael Cude, College Grove, TN (US)

(73) Assignee: Coeur, Inc., Lebanon, TN (US)

( * ) Notice: Subject to any disclaimer, the term of this patent is extended or adjusted under 35 U.S.C. 154(b) by 539 days.

(21) Appl. No.: 11/759,694

(22) Filed: Jun. 7, 2007

(65) Prior Publication Data

US 2008/0302697 A1 Dec. 11, 2008

(51) Int. Cl.
*B65D 43/00* (2006.01)
*B65D 21/02* (2006.01)

(52) U.S. Cl.
CPC .................................. *B65D 21/0204* (2013.01)
USPC ........ 206/557; 206/363; 220/23.4; 220/23.83

(58) Field of Classification Search
USPC .......... 206/1.5, 820, 557–560, 562–563, 363; 220/23.4, 23.2, 23.8, 23.83, 23.86
See application file for complete search history.

(56) References Cited

U.S. PATENT DOCUMENTS

| | | | | |
|---|---|---|---|---|
| 3,419,176 | A * | 12/1968 | Lipfert et al. ................. | 220/23.4 |
| 4,133,445 | A * | 1/1979 | Mandelbaum ............... | 220/23.4 |
| 4,355,755 | A | 10/1982 | Faller | |
| 4,656,840 | A * | 4/1987 | Loofbourrow et al. ......... | 62/530 |
| 4,770,297 | A * | 9/1988 | Chang ............................. | 206/379 |
| 4,919,268 | A * | 4/1990 | Young et al. ................... | 206/509 |
| 5,333,733 | A * | 8/1994 | Murata .......................... | 206/714 |
| 5,381,916 | A * | 1/1995 | Strawder ....................... | 220/23.4 |
| 5,447,249 | A * | 9/1995 | Vickers ....................... | 220/23.83 |
| 5,709,304 | A * | 1/1998 | Credle, Jr. ...................... | 206/501 |
| 6,418,861 | B1 | 7/2002 | Flam | |
| 6,896,141 | B2 * | 5/2005 | McMichael et al. .......... | 206/571 |
| 2002/0079313 | A1 * | 6/2002 | Grayson ....................... | 220/23.4 |
| 2003/0141300 | A1 * | 7/2003 | French .......................... | 220/23.4 |
| 2006/0091030 | A1 * | 5/2006 | Tawanapoor ................. | 206/320 |

FOREIGN PATENT DOCUMENTS

| | | |
|---|---|---|
| JP | 06-052492 U | 7/1994 |
| JP | 10-001139 A | 1/1998 |

OTHER PUBLICATIONS

Search Report and Written Opinion for corresponding PCT International Application No. PCT/US2008/065330, dated Sep. 30, 2008.

* cited by examiner

*Primary Examiner* — Anthony Stashick
*Assistant Examiner* — Robert Poon
(74) *Attorney, Agent, or Firm* — Hahn, Loeser & Parks, LLP

(57) ABSTRACT

A container for packaging associated articles includes coupling members fashioned on one or more sides of the container for interconnecting a plurality of containers together. The coupling members may be integrally fashioned with the containers and may comprise raised ribs and recessed channels for press fitting the adjacently placed containers together.

6 Claims, 5 Drawing Sheets

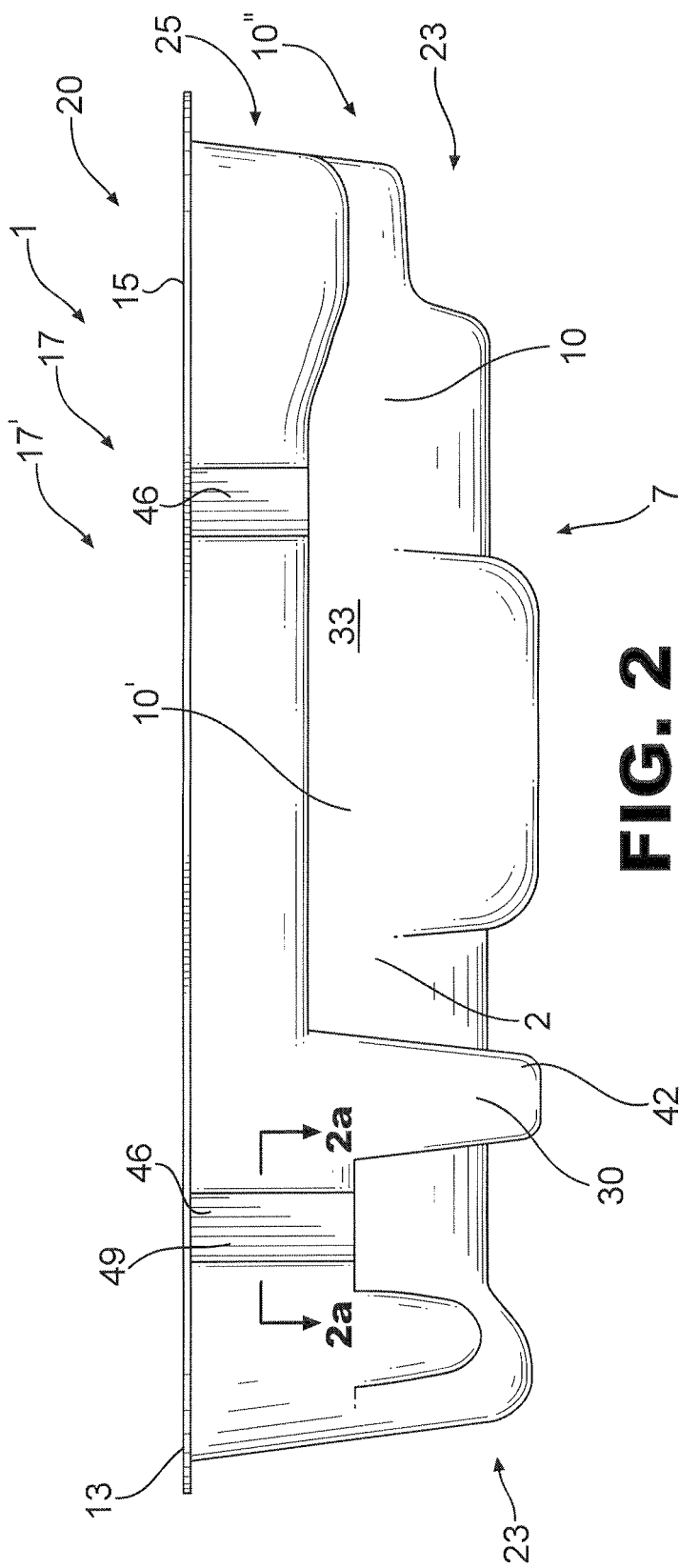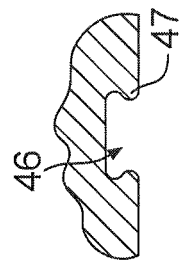

DUAL PACK CONTAINER

TECHNICAL FIELD

The present invention pertains to containers for packaging articles, which may be sterile articles used in the medical industry, and more particularly, to similar or substantially identical containers that can be connected together and disconnected without the use of additional fasteners.

BACKGROUND OF THE INVENTION

The medical industry extensively utilizes plastic molded articles, such as syringes for example, for various medical procedures and treatments. It is crucial that these articles be manufactured and packaged in a sterile environment to ensure safe and effective treatment for the patient. Accordingly, molded articles like the syringe may be placed in a tray and sealed until needed for use at the appropriate time.

A power injector is one example of a device that uses sterile syringes to inject fluids into a patient at controlled rate and/or pressure. A motor-driven ram advances the syringe plunger in a controlled manner. These types of injectors are often loaded with sterile empty syringes and are filled by drawing fluid into the syringe from a supply via the plunger assembly. In some circumstances, the power injector is loaded with pre-filled syringes. In either case, the syringes used are disposed of after use.

During certain procedures, it is often necessary to use multiple syringes when different fluids are being injected into the patient. The syringes may be of the same size and type. It would be advantageous to have pre-packaged syringes that could be used in any quantity without breaking the sterile field of the unused syringes. The embodiments of the present invention obviate the aforementioned problems.

BRIEF SUMMARY

One embodiment of subject invention includes a tray for storing associated articles comprising a base having first and second tray wall portions terminating at the base of the tray. The tray may further comprise a first coupling member extending from the first tray wall portion and a second matching coupling member extending from the second tray wall portion, where the first coupling member is configured to match the second coupling member.

In one aspect of the embodiments of the present invention the first and second tray wall portions terminate at distal ends of the tray base. The base and the first and second tray wall portions may be rigid or semi-rigid.

Another embodiment of the present invention contemplates first and second tray wall portions that terminate at proximal ends of the tray base.

In another aspect of the embodiments of the present invention the first coupling member of the tray includes an interlocking recess and the second coupling member includes a matching interlocking protrusion. The interlocking recess and protrusion may be extended from and/or integrally formed with the wall portions of the tray.

In yet another aspect of the embodiments of the present invention the tray is a unitary tray constructed of a moldable polymer like plastic. By unitary it is meant that the tray is not constructed or assembled from multiple components but may be molded, by thermoforming for example, as a singular component.

In another embodiment a container for storing associated articles includes a container base, at least first and second container walls extending from the container base, a first interlocking recess extending from the first container wall and a second interlocking protrusion extending from the at least a second container wall where the first interlocking recess is contoured to match the second interlocking protrusion for connecting to another associated container having similar interlocking components. The container also includes a cover for enclosing associated articles within the container.

In one aspect of the embodiments of the present invention, the container base and the first and second container walls define a container opening where the cover may be affixed to the container opening for sealing the associated articles.

Another aspect of the embodiments of the present invention includes first and second container walls that extend from distal ends of the container base.

In yet another aspect of the embodiment of the present invention, the first and second container walls are tapered with respect to the container opening. The first interlocking recess and the interlocking protrusion may be offset from a centerline of the container. The first interlocking recess may be offset a distance D in a first direction and the second interlocking protrusion may be substantially offset a distance D in a second direction.

In still another aspect of the embodiment of the present invention, the container may include a third and at least a fourth coupling member, which may be positioned on opposite sides of the container.

BRIEF DESCRIPTION OF THE DRAWINGS

FIG. 2 is a perspective view of a second side of a container according to the embodiments of the present invention.

FIG. 2a is a planar cutaway view of a channel fashioned in the container according to the embodiments of the present invention.

DETAILED DESCRIPTION OF THE INVENTION

Figure 1:
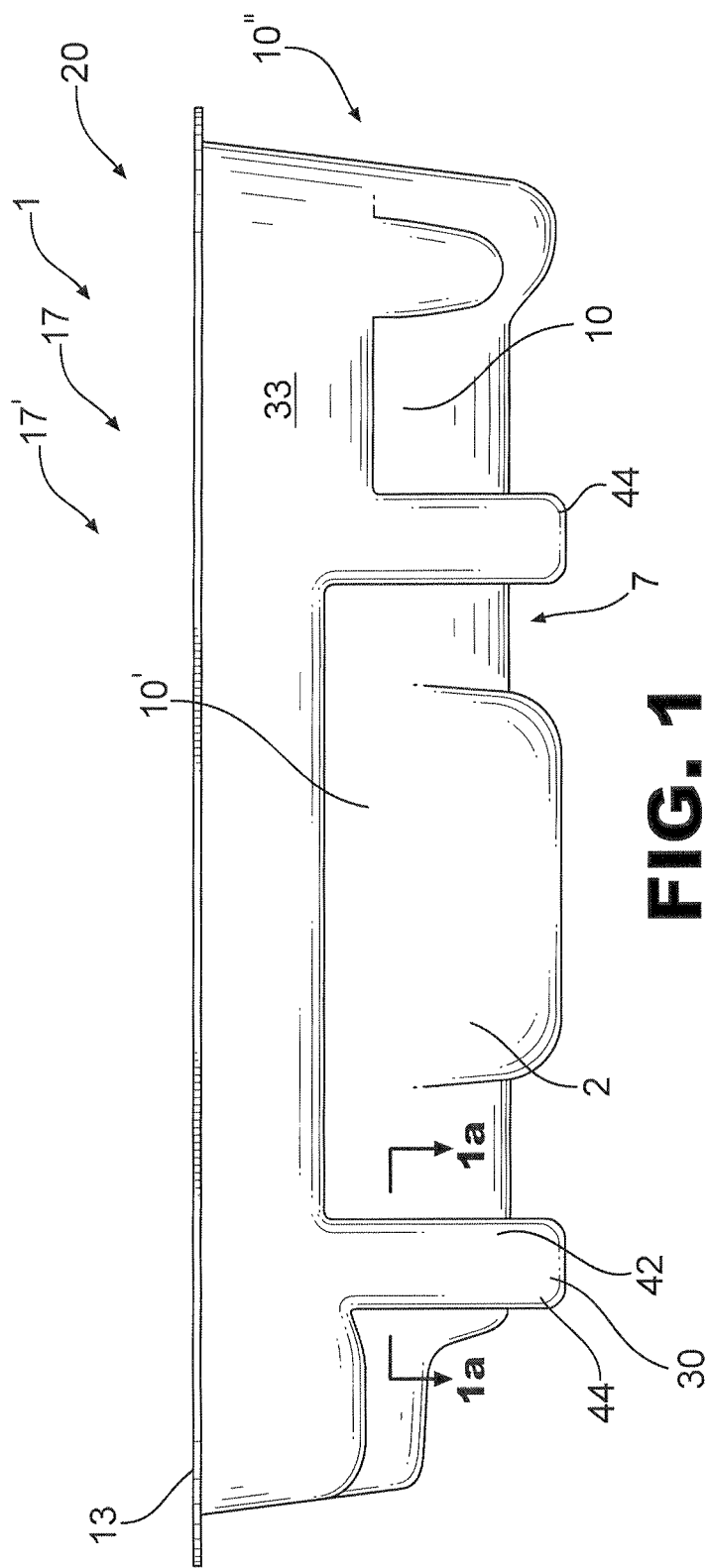
FIG. 1 is a perspective view of a first side of a container according to the embodiments of the present invention.

Referring now to the drawings wherein the showings are for purposes of illustrating embodiments of the invention only and not for purposes of limiting the same, FIGS. 1 and 2 show a container for storing an associated article depicted generally at 1. The container 1 may be constructed to match the shape of the associated article stored therein. In one embodiment, the container 1 may manufactured to receive, for example, a medical device such as a syringe. In this example, the interior surface of the container 1 may be fashioned having a narrow region at one end for cradling the syringe tip. Similarly, the distal end may be disk shaped for receiving the syringe plunger handle. However, it will be understood by persons of ordinary skill in the art that the interior of the container 1 may be contoured in any manner for packaging any type and/or shape of article as chosen with sound judgment. Accordingly, the container 1 may include a base 7 or base portion 7 positioned generally at the bottom of the container 1. Walls 10 or wall portions 10 may extend upward from the base 7 and terminate at a container rim 13. The container rim 13 or rim 13 may comprise a ledge 15 projecting outwardly at an acute angle with respect to the walls 10, the periphery of which may define an open end 17' of the container 1 through which the packaged article may be inserted and/or removed. A cover 20 may extend across the opening 17 of the container 1 to seal the components within the container 1 from exposure to ambient conditions and/or contamination. The container 1 may be generally rectangular in configuration having longer walls 10' spaced apart by shorter walls 10" each terminating at the base 7. Other geometric configurations are also contemplated including but not limited to square, circular or oval configurations. Additionally, asymmetrical configurations are also contemplated by the embodiments of the present invention.

With continued reference to FIGS. 1 and 2, the container 1 may therefore include a tray 2, comprising contoured walls 10 and the base 7, and a cover 20 extending around the ledge 15 thereby covering the tray opening 17. The tray 2 may be constructed of a polymer material like HIPS (High Impact Polystyrene), PVC (Polyvinyl Chloride), Polypropylene or Polyethylene or other material including but not limited to PET (Polyethylene Terephthalate). It is contemplated that other types of material may also be used like, for example, metal and more specifically stainless steel. However, any material, polymer or otherwise, may be utilized for constructing the tray 2 as is appropriate for use with the various articles stored within the container 1. One method of forming the tray 2 may be accomplished by the process of thermoforming. This process utilizes a mold having a mold cavity fashioned in a particular shape, for example like that described above for the syringe. The thermoforming process heats sheet plastic and forms it into and/or over the mold. The process may utilize vacuum, air pressure and/or mechanical forming assists to move the softened plastic in contact with the shape of the forming mold. Another method of forming the trays may include plastic injection molding. Still other methods may include metal forming and/or metal fabricating techniques. However, any process may be used to construct the tray 2 as chosen with sound engineering judgment. After insertion of the article into the tray 2, which may be a syringe, the cover 20 may placed onto the ledge 15 thereby spanning the container opening 17. The cover 20 may be applied or affixed to the ledge 15. Securing the cover 20 to the ledge 15 may include the use of a substance that holds the cover 20 in place, which may be an adhesive. Fasteners may also be used to hold the cover 20 in place. Although, any material and/or process of securing the cover in place may be utilized as chosen with sound engineering judgment. The cover 20 may be substantially transparent or translucent and may be generally flexible. The cover material may be strong, and in particular, difficult to tear allowing vapor, but not liquid, to permeate the surface thereof. One type of cover material, for example, that may be used is Tyvek® manufactured by the Dupont® Company. However, the cover may be constructed from any material as is appropriate for use with the embodiments of the present invention. It is noted here that the process of forming the tray 2, inserting the article and applying the cover 20 may be conducted in a clean environment, which may be a room filtered from air born material, other contaminants, humidity and the like. The tray 2 may be placed in a chamber and enveloped by a sterilizing gas or vapor for sterilizing the tray 2 and its contents. In this manner, when the article is needed, the operator may separate the container 1 from an adjacent container, as will be discussed further in a subsequent paragraph, and remove the cover 20 thereby exposing a sterile article for use by the operator.

Figure 3:
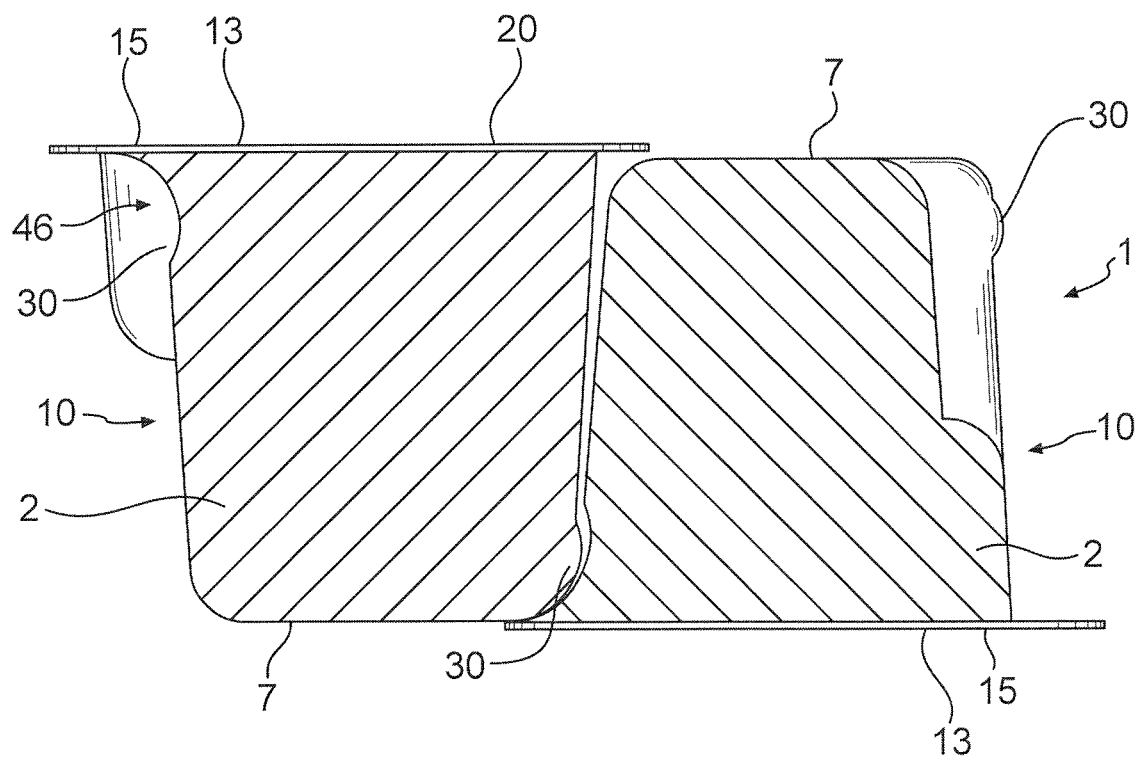
FIG. 3 is a cutaway view of two containers connected together according to the embodiments of the present invention.

With continued reference to FIGS. 1 and 2 and now to FIG. 3, the wall portions 10 may further include coupling members 30 for connecting the tray 2 to another object. In one embodiment, the coupling members 30 may be used to connect the tray 2 to another similar or substantially identical tray 2 which, in one embodiment, may have corresponding or matching coupling members 30. That is to say that the coupling members 30 of the tray 2 may be used to connect two of more of the same kind of tray 2 together. This is especially helpful in a situation where an end user, which may be a medical technician, over time utilizes numerous articles of the kind stored in the containers 1 but may only require one article for a specific procedure. Accordingly, the medical technician may detach the number of individually packaged syringes required for the procedure leaving the remaining the syringes grouped together without breaking the sterile field. While the present embodiment discusses connecting similar or substantially identical containers 2 together, it is contemplated in an alternative embodiment that the coupling members 30 may be used to connect trays 2 of substantially different configurations, which may include trays having different shapes. As long as the coupling members 30 of the differently configured trays 2 match, any type and/or quantity of containers 1, similar or dissimilar, may be connected together. Still, the coupling members 30 may be used to connect the tray 2 to any object chosen with sound judgment as is appropriate for use with the embodiments of the present invention.

With continued reference to FIGS. 1 through 3, in one embodiment the coupling members 30 may be integrally fashioned into the wall portions 10 of the tray 2. By integrally fashioned into the wall portions 10 it is meant that the coupling members are not distinct objects affixed to the wall portions 10 but rather the coupling members 30 and the wall portions 10 are fashioned together as a singular unit. The coupling members 30 may extend from the face 33 of the wall portions 10, either outwardly or inwardly. In the embodiment where the tray is thermoformed or injected molded, the mold may include contoured cavities that define the shape of the wall portions 10 and coupling members 30. In this way, the coupling member 30 is formed integrally with and at the same time as the wall portions 10 of the tray 2. Other embodiments are contemplated where separately constructed coupling members 30 are attached to faces of the wall portions 10.

Figure 1A:
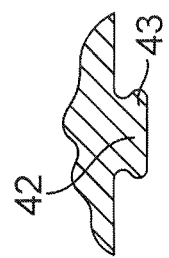
FIG. 1a is a planar cutaway view of a protrusion extending from the container according to the embodiments of the present invention.
Figure 4:
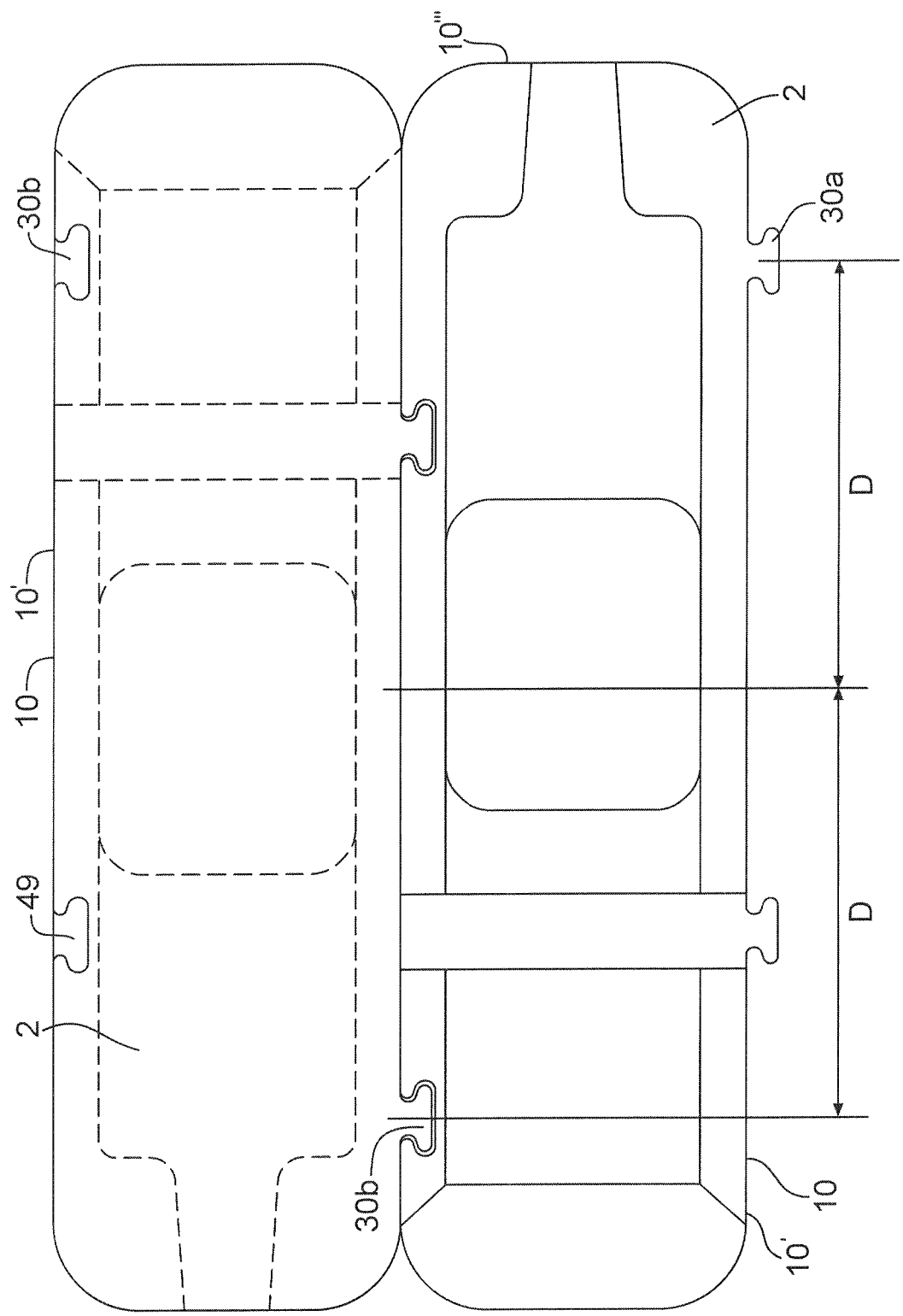
FIG. 4 is schematic representation of two containers connected together according to the embodiments of the present invention.
Figure 5:
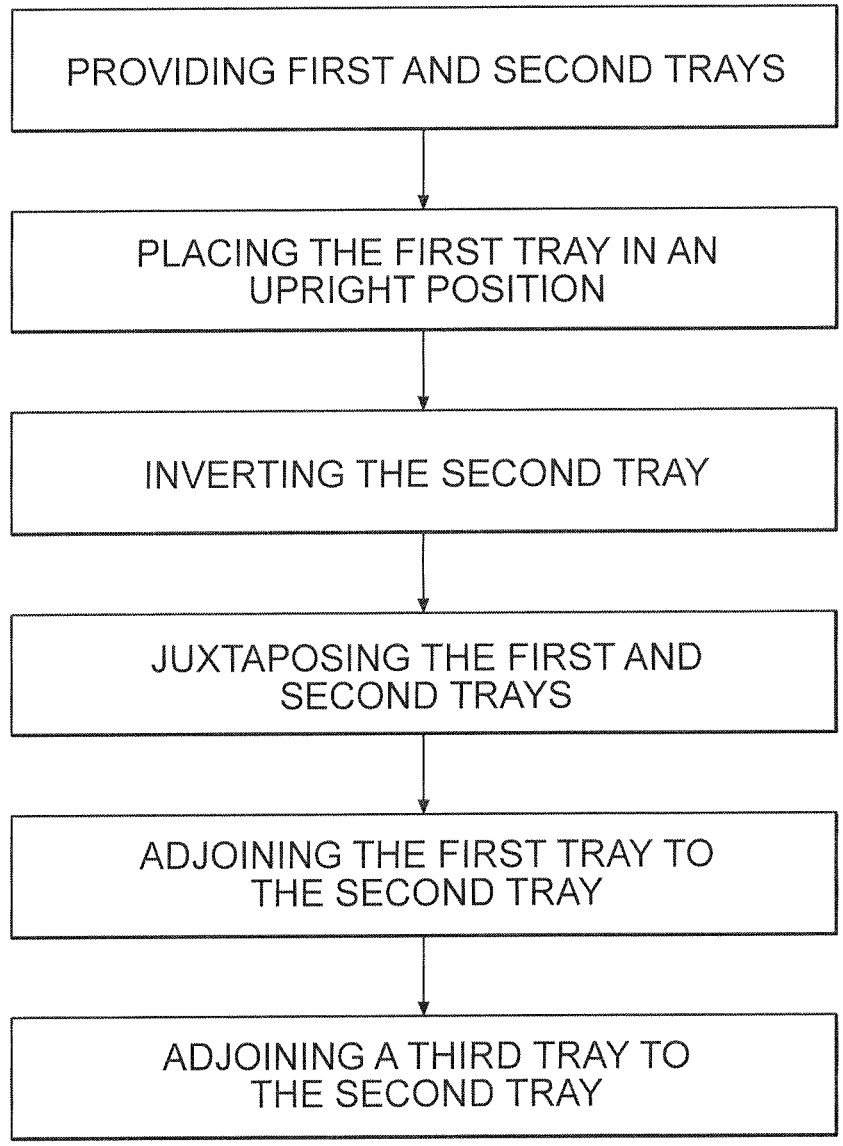
FIG. 5 is flow chart of the method of packaging trays according to the embodiments of the present invention.

With reference to FIGS. 1a and 2a and also to FIGS. 3 and 4, different configurations of coupling members 30 may be included with the tray 2. More specifically, a first coupling member, which may be a male coupling member 30a, may be fashioned within one wall portion 10 and a second coupling member, which may be a matching female coupling member 30b, may be fashioned in another wall portion 10. It will be readily seen that the male coupling member 30a of one tray 2 may be interconnected with the female coupling member 30b of another associated tray 2 thereby facilitating the connecting of numerous containers 1. In one embodiment, the first coupling member may include an interlocking protrusion 42. Likewise, the second coupling member may include an interlocking recess 46. The interlocking protrusion 42 may include a first edge portion 43 that engages a lip 47 of the interlocking recess 46. It follows that as the material of the tray 2 may be constructed from an elastically deformable material, the first and second coupling members of separate containers 1 may be interconnected via an interference fit. In other words, the first coupling member of a first container 1 may be pressed together or snapped into engagement with the second coupling member of another container 1.

Multiple coupling members 30 may be fashioned on the exterior of the wall portions 10. In one embodiment, the coupling members 30 may include multiple individual interlocking protrusions 42 and interlocking recesses 46 positioned with respect to a centerline axis of the tray 2. The centerline axis C may be a longitudinal or a transverse centerline axis. However, any axis may be chosen from which to position the coupling members as chosen with sound judgment. The interlocking protrusions 42 may be positioned a distance D away from the centerline in a first direction. Similarly, the interlocking recesses 46 may be positioned distance D away from the centerline a second opposite direction. In this manner, individual coupling members 30 may correspondingly be staggered on the same side or on opposite sides of the tray 2 so that when two trays 2 are juxtaposed the interlocking protrusions 42 of one tray 2 will align with the interlocking recesses 46 on the other tray 2. It is noted that any quantity of individual coupling members 30 may be positioned at any distance or distances with respect to a centerline axis as is appropriate for use with the embodiments of the subject invention.

With reference again to FIGS. 1 and 2, the coupling members 30 may be contiguously formed along the exterior of the tray 2. In particular, the interlocking protrusion 42 may comprise a raised rib 44 extending along a distance of the wall portion 10 on the exterior of the tray 2. Similarly, the interlocking recess 46 may form a channel 49 also extending through a distance along the wall portion 10. It is noted here that any length, width or height of the rib 44 and/or channel 49 may be chosen as is appropriate for use with various configurations of the tray 2. In connecting the trays 2 together, the packager may invert one tray 2 with respect to another, as will be discussed in detail in a subsequent paragraph, align the raised ribs 44 and channels 49 and press fit the trays 2 together whereby the edge portions 43 snap into the lips 47 in an interference fit. While the raised ribs 44 and channels 49 are depicted in the figures to traverse the tray 2 with respect to its longitudinal axis, it is contemplated in an alternate embodiment that longitudinally fashioned ribs 44 and channels 49 may be incorporated into the tray 2. However, any configuration of the coupling members 30 may be used to interconnect the trays 2.

With reference again to FIG. 3, as discussed above the walls 10 or wall portions 10 may terminate as distal ends of base 7. In one embodiment, the walls portions 10 may be tapered at the base 7 of the tray 2. That is to say that the wall portions 10 may extend progressively outward as the wall portions 10 proceed upwardly toward the rim 13 forming a generally trapezoidal cross-section. In order to efficiently store the tapered trays 2, the coupling members 30 may be configured so that the interlocking protrusions 42 align with the interlocking recesses 46 when one tray 2 is inverted with respect to another tray 2. This maximizes storage space as the trays 2 are placed into a packaging container by minimizing and/or eliminating wasted space between the trays 2. In this manner, more trays 2 can be packaged into the same size container. It will be appreciated by persons of ordinary skill in the art that other cross sectional configurations may be chosen without departing from the intended scope of coverage of the embodiments of the present invention.

With reference to all of the FIGURES, packaging of the trays 2 will now be discussed. Once multiple trays 2 have been formed, the associated article for which the tray 2 is fashioned may be inserted into the tray 2 and the tray 2 enclosed by the cover 20 thus forming a container 1 for storing or packaging associated articles. The containers 1 may then placed onto a packaging surface and snapped together wherein the coupling members 30 of one container 1 fit together with the coupling members of an adjacent container 1. In one embodiment, the each subsequent container 1 may be inverted with respect to the previous container 1. The containers 1 may then be delivered to the end user for detaching only the quantity of the articles needed for a particular activity or procedure.

The invention has been described herein with reference to the preferred embodiment. Obviously, modifications and alterations will occur to others upon a reading and understanding of this specification. It is intended to include all such modifications and alternations in so far as they come within the scope of the appended claims or the equivalence thereof.

What is claimed is:
1. A container for storing associated articles, comprising:
a container base;
first and second container walls extending from opposing sides of the container base;
a rim disposed about the first and second container walls opposite the container base;
where the container base and the first and second container walls at least partially defining a storage volume having a container opening for receiving an article for storage within the volume, the rim surrounds said container opening, and the first and second container walls extending outwardly toward the rim tapering from the rim toward the base,
a first interlocking member forming a recess within the first container wall extending between the base and the rim;
a second interlocking member forming a protrusion extending from the at least a second container wall between the base and the rim;
wherein the first interlocking member is configured to substantially interlock with the second interlocking member for connecting the container in juxtaposed relation to a second container having the same arrangement of first and second interlocking members with the container base of the container being co-planar with the rim of the second container,
a third interlocking member forming a recess within the first container wall extending between the base and the rim; and
a fourth interlocking member forming a protrusion extending from the at least a second container wall between the base and the rim;
wherein the third interlocking member is configured to substantially interlock with the fourth interlocking member for connecting the container in juxtaposed relation to the second container having the same arrangement of third and fourth interlocking members with the container base of the container being co-planar with the rim of the second container,
where, the first and second interlocking members are equidistant from, in opposite directions, an axis through the middle of the a first and the at least a second container walls, and where the third and the fourth interlocking members are equidistant from, in opposite directions, the axis;
where the first and third interlocking members extend from the rim toward the container base and the second and fourth interlocking members extend from a container wall adjacent the container base toward the rim; and
where the first and third interlocking members are integrally fashioned into the container walls.

2. The container as defined in claim 1, wherein a cover for enclosing sterile articles within the container is secured to the rim for sealing the associated articles.

3. The container as defined in claim 2, wherein the cover is vapor permeable but restricts the flow of liquid into the container.

4. The container as defined in claim 1,
wherein the first and second interlocking members are offset the same distance in opposing directions from a centerline of the container, the centerline extending transversely between the first and at least a second container walls, and,
wherein the third and fourth interlocking members are offset the same distance in opposing directions from the lateral centerline of the container, the distance by which the third and fourth members are offset being different than the distance by which the first and second members are offset.

5. The container as defined in claim 1, wherein the first and second interlocking members are offset in opposing directions from a central plane extending between the first and second sides and laterally therefrom, the plane being positioned midway between the container base and the container opening, and wherein the third and fourth interlocking members are offset in opposing directions from the central plane.

6. The container as defined in claim 5, wherein the first, second, third, and fourth interlocking members are offset generally the same distance from the central plane.

* * * * *